United States Patent
Miyake et al.

(10) Patent No.: US 6,197,255 B1
(45) Date of Patent: Mar. 6, 2001

(54) CHEMICAL ANALYZING APPARATUS

(75) Inventors: Ryo Miyake, Tsukuba; Yoshihiro Nagaoka, Ishioka; Akira Koide, Ibaraki-ken; Naruo Watanabe, Ibaraki-ken; Yasuhiko Sasaki, Ibaraki-ken; Hajime Kato, Ibaraki-ken; Takao Terayama, Ushiku; Hiroshi Mitsumaki, Mito; Hiroyasu Uchida; Takeshi Shibuya, both of Hitachinaka; Yasuhiro Yoshimura, Ibaraki-ken, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/398,046

(22) Filed: Sep. 17, 1999

(30) Foreign Application Priority Data

Sep. 18, 1998 (JP) .................................................. 10-264306

(51) Int. Cl.⁷ .................................................. G01N 35/02
(52) U.S. Cl. ............................... 422/64; 422/63; 422/67; 422/100; 422/103; 436/43; 436/47; 436/49; 436/54; 436/180; 134/21; 134/22.11; 134/24; 134/26; 134/37
(58) Field of Search .................. 422/63, 64, 67, 422/100, 103, 104; 436/43, 47, 49, 54, 180; 134/21, 22.11, 24, 26, 37, 169 R

(56) References Cited

U.S. PATENT DOCUMENTS

| | | | |
|---|---|---|---|
| 4,346,056 | * | 8/1982 | Sakurada ................................ 422/64 |
| 4,451,433 | * | 5/1984 | Yamashita et al. ..................... 422/63 |
| 4,844,868 | * | 7/1989 | Rokugawa ............................. 422/64 |
| 5,173,741 | * | 12/1992 | Wakatake .............................. 356/246 |
| 5,192,505 | * | 3/1993 | Sakagami .............................. 422/64 |
| 5,232,664 | * | 8/1993 | Krawzak et al. ...................... 422/64 |
| 5,336,062 | * | 8/1994 | Richter ............................. 417/413 A |
| 5,424,036 | * | 6/1995 | Ushikubo .............................. 422/64 |
| 5,424,212 | * | 6/1995 | Pinsl-Ober et al. ................... 436/50 |
| 5,434,083 | * | 7/1995 | Mitsumaki et al. ................... 436/48 |
| 5,519,635 | * | 5/1996 | Miyake et al. ...................... 364/497 |
| 5,529,465 | * | 6/1996 | Zengerle et al. .................. 417/413.2 |
| 5,736,100 | * | 4/1998 | Miyake et al. ........................ 422/64 |
| 5,789,252 | * | 8/1998 | Fujita et al. ........................... 436/49 |
| 5,948,358 | * | 9/1999 | Saito .................................... 422/64 |

FOREIGN PATENT DOCUMENTS

| | | | |
|---|---|---|---|
| 195 34 955 A1 | 3/1996 | (DE) . |
| 198 37 434 A1 | 3/1999 | (DE) . |
| 198 42 953 A1 | 4/1999 | (DE) . |
| 198 49 591 A1 | 5/1999 | (DE) . |

* cited by examiner

*Primary Examiner*—Jeffrey Snay
*Assistant Examiner*—Patricia Kathryn Bex
(74) *Attorney, Agent, or Firm*—Antonelli, Terry, Stout & Kraus, LLP

(57) ABSTRACT

A chemical analyzing apparatus comprises a reaction cell holder which holds a plurality of reaction cells that are supplied with samples and reagents at a predetermined position, a measurer for measuring characteristics of the sample, a plurality of reagent containers, a liquid deliverer provided below each of the plurality of reagent containers, one or more sound wave generators provided outside the reaction cells, and storage containers for storing cleansing liquid with different contamination states. The cleansing liquid with different contamination states is reused according to the contamination levels of the reaction cells.

5 Claims, 8 Drawing Sheets

CHEMICAL ANALYZING APPARATUS

BACKGROUND OF THE INVENTION

Field of the Invention

The present invention relates to a chemical analyzing apparatus that determines the kind and concentration of a substance dissolved in a liquid and more particularly to a chemical analyzing apparatus that analyzes components of humor and water.

Among conventional chemical analyzing apparatus is a chemical analyzing apparatus of U.S. Pat. No. 4,451,433. This chemical analyzing apparatus comprises a calorimetric unit for analyzing and determining protein and enzyme contained in blood and components of urine and an ion analyzing unit for analyzing ions in blood. This chemical analyzing apparatus has a processing rate of several hundred tests per hour and, in a large type, 9000 tests or more per hour. The colorimetric unit in particular has a large number of reaction containers or cells placed on a circumference of a turntable mounted on the upper surface of an apparatus body and performs overlap processing to mix, react and measure samples successively.

This apparatus comprises: an automatic sample/reagent supply mechanism for supplying samples and reagents to reaction cells; a holder for holding several tens of kinds of reagent containers; an automatic agitation mechanism for agitating the samples and reagents in the reaction cells; a measuring device for measuring characteristics of the samples during or after reaction; an automatic cleansing mechanism for drawing by suction and discharging the samples after characteristic measurements are made and for washing the reaction cells; an automatic cleansing mechanism for washing the automatic sample/reagent supply mechanism; and a controller for controlling the operations of these mechanisms and devices.

There are several tens of kinds of colorimetric test items and, even in normal assays, each sample is tested for at least about ten kinds of inspection items. Conventional reagent supply mechanisms use a reagent pipetting mechanism. The reagent pipetting mechanism comprises mainly a nozzle for drawing reagent into it and holding the reagent there, a mechanism for moving the nozzle three-dimensionally, and a suction/delivery control pump for drawing and discharging the reagent into and out of the nozzle.

To transmit the suction/delivery operation of the pump to the nozzle with good response, pure water (hereinafter referred to as system water) is filled in a pipe between the pump and the nozzle. The system water and the reagent are separated by air to avoid their mixing. This air layer is formed by drawing air into the nozzle before drawing the reagent into it.

The supply of reagent is performed in the following manner. First, the nozzle is dipped into a reagent container by a three-dimensional transfer mechanism to draw by suction a specified amount of reagent into it. The nozzle is moved away from the reagent container and placed over a reaction cell into which the reagent is discharged. After the reagent is discharged, the interior and exterior of the nozzle is washed with cleansing liquid in a nozzle washing bath to avoid contaminating the next reagent. Because the path which the nozzle of the reagent pipetting mechanism travels is fixed, a holder for holding the reagent containers is provided below the path of the nozzle.

Another example of the conventional technology is an automatic analyzing apparatus described in JP-A-63-131066. This example is similar to the above-described conventional technology in terms of sampling, mixing and reaction, photometry, and the washing of reaction cells but differs from it in the reagent supply method.

With a reduction in apparatus size taken as the first objective, this conventional technology arranges the reagent container holder above the reaction cell holder so that the reaction cells and the reagent containers overlap at two predetermined points. Hence, the delivery of reagent into the reaction cell is done by a piston formed integral with the side surface of each reagent container. The piston is actuated by a piston rod actuator provided at a reagent delivery position.

At the delivery position, the piston rod actuator for the reagent container is temporarily connected to the piston rod. Next, the piston rod is pulled up to draw the reagent from the reagent container into the piston. When it reaches the upper limit of its stroke, the piston rod meshes with a gear that rotates the piston through 180 degrees. At this time, the rotation of the piston closes a hole which was open to draw in the reagent, and opens a hole connecting to a delivery port. As the piston rod is driven down, the reagent in the piston is discharged through the hole into the reaction cell.

The above-mentioned conventional technology has the following three drawbacks.

First, the reduction in the size of the apparatus and in the space required is not sufficient. Second, contamination between different reagents cannot be prevented completely. Third, the amount of pure water used is large, requiring a pure water making device outside the apparatus and periodical replacement of the filter and other components, which in turn necessitates additional costs and installation space. These problems are described in detail as follows.

The reason that the reduction in size and space is difficult in the conventional technologies will be explained. The first conventional technology described above picks up a sample and a reagent by the pipetting mechanism, which requires all elements associated with the operations, such as sampling, washing, suction and discharge, to be arranged on a plane beneath the movement locus of the pipetter nozzle. To avoid interference among elements, a certain degree of space is required. Furthermore, the fact that these two-dimensionally arranged elements are large in numbers and kinds also contributes to hindering a reduction in size.

A similar problem also exists as to the reduction in a space around the agitation mechanism. The conventional technology performs stirring with spatulas and thus requires a cleansing device for spatulas. It is also necessary to install the cleansing device so that it does not interfere with the movement locus of the spatulas, making the space reduction difficult. Because the reagent pipetting mechanism and the agitation mechanism using spatulas are employed, there are limitations to the relative positions among the elements, which makes it impossible to adopt a compact arrangement, rendering the size reduction difficult.

The second conventional technology crosses the reagent holder and the reaction cell holder to realize a certain degree of size reduction. With the agitation mechanism, however, the situation is no better than the first conventional technology and, when the apparatus is considered as a whole, the size reduction is not satisfactory.

Next, the problem of mutual contamination will be described. The mutual contaminations occur because different samples and reagents are handled by a common supply means.

The first conventional technology has a sampling mechanism that draws in and discharges, or pipettes, samples successively with a single nozzle. Further, the mutual contamination is also likely to occur in the reagent pipetting mechanism that pipettes several tens of reagents with a single nozzle and in the agitation mechanism that stirs the samples and reagents in the reaction cells.

The reaction cells can be thoroughly washed clean because after photometry they are washed with a cleansing liquid a plurality of times. As to the sample and reagent nozzles and the agitation mechanism, because they are washed in as short a duration of time as one cycle, thorough cleansing is difficult. In the case of biochemistry in particular, mutual contaminations by residual reagents have a significantly greater effect on the result of assay than residual samples.

Therefore, the essential point is the prevention of mutual contamination from the nozzle of the reagent pipetting mechanism and the spatulas of the agitation mechanism. In the second conventional technology a reagent delivery pump is provided for each reagent cell to prevent the mutual contamination by the reagent supply system. However, the agitation mechanism employs a conventional mechanism using spatulas and still has a problem of mutual contamination.

The next problem to be solved is a reduction in the amount of pure water used and simplification of associated facilities. The pure water is used mostly as a cleansing liquid as described in the explanation of the second problem. Hence, reducing the amount of cleansing liquid will result in a significant reduction in the amount of pure water used. With the conventional technologies, however, a large amount of cleansing liquid needs to be used to prevent the mutual contamination. The nozzles of the sampling mechanism and the reagent pipetting mechanism and the spatulas of the agitation mechanism, in particular, are washed with an increased flow of cleansing liquid in order to improve the cleansing capability and thereby complete the washing operation in a short period of time.

The necessity to ensure the required analyzing performance does not allow the cleansing liquid to be reduced in amount. The required amount of pure water at present is several tens of liters per hour. To meet this requirement a pure water making device of filter type is installed separately outside the apparatus and connected through water piping to the apparatus. The pure water making device and its associated piping require additional space and costs the user additional initial investments. Maintaining the pure water making device requires periodical replacement of expensive filters, which is a substantial burden for the user.

OBJECT AND SUMMARY OF THE INVENTION

A first object of the present invention is to provide a chemical analyzing apparatus with small size and reduced space. A second object is to provide a chemical analyzing apparatus that prevents mutual contamination among samples and reagents. A third object is to provide a chemical analyzing apparatus which uses a small amount of pure water and requires no associated facilities outside the apparatus, such as a pure water making device, or places to install such facilities.

These objectives can be realized by an apparatus which comprises: a reaction cell holder for holding a plurality of reaction cells, at predetermined positions, to which samples and reagents are supplied; a measuring means for measuring characteristics of the samples; a plurality of reagent containers; and a liquid delivery means, a sound wave generating means and a recovery container, all installed below the reagent containers, the liquid delivery means corresponding to the individual reagent containers, the sound wave generating means installed outside the reaction cells for generating sound waves toward the reaction cells, the recovery containers holding cleansing liquid recovered according to the cleansing state.

DESCRIPTION OF THE EMBODIMENTS

Figure 1:
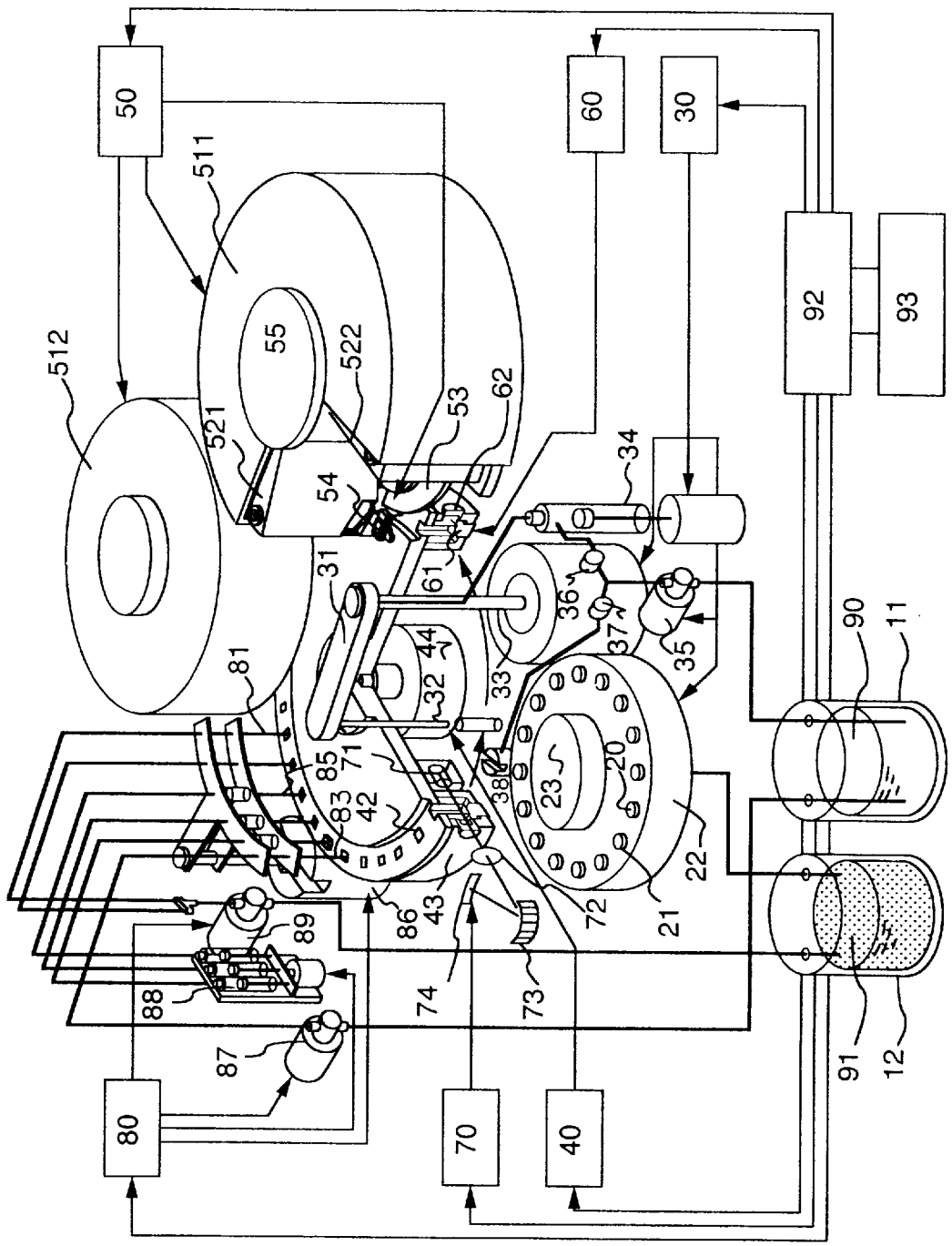
FIG. 1 is a schematic diagram showing the configuration of the chemical analyzing apparatus according to the present invention.

The construction of one embodiment of the chemical analyzing apparatus according to the present invention will be described by referring to FIGS. 1 to 5. FIG. 1 is a perspective view showing the overall configuration of the apparatus of the invention.

This analyzing apparatus comprises roughly nine elements or units: a reaction disc unit for holding and moving the reaction cells; followings are provided around the reaction disc unit while the reaction disc unit play a center, a sample supply unit (represented by reference numbers 30s); a first reagent supply unit (represented by reference numbers 50s); a second reagent supply unit; a reaction cell cleansing mechanism (represented by reference numbers 80s); a spectrophotometer unit (represented by reference numbers 70s); and a control unit for applying control signals to these elements or units. It also includes a controller 92 for issuing operation instructions to each control unit and a central signal processor 93 for inputting data, outputting control signals, calculating signals, outputting calculated signals and recording.

The sample supply unit includes test tubes 21 containing samples 20, and a sample holder 22 for holding the test tubes 21 on its circumference. At a predetermined position by the side of the sample holder 22 there is provided a sample pipetter 31 that draws in the samples 20 and supplies them into the reaction cells 41. The amount of samples supplied from the sample pipetter 31 in this embodiment to the reaction cells 41 is approximately 1–10 $\mu l$.

The sample pipetter 31 has a nozzle 32 for drawing in a sample and holding it therein, a 3-dimensional drive mechanism 33 for lifting and rotating the nozzle, and a syringe type pump 34 for drawing the sample into the nozzle and delivering the sample from the nozzle.

The syringe type pump 34 is connected through a pipe with a liquid delivery pump 35 that supplies the system water. In the middle of the pipe there is a first solenoid valve 36 for controlling the supply of the system water. The liquid delivery pump 35 is connected with another pipe which branches toward a washing tank 38 for the nozzle. This pipe has a second solenoid valve 37 partway along its length for controlling the pipe communication. The washing tank 38 is connected to a waste liquid tank 91 via a waste liquid pipe.

A rotary drive mechanism 23 rotates the sample holder 22 to move a target test tube 21—which should supply a sample to a reaction cell 42—immediately below the nozzle 32 of the sample pipetter 31. Signal lines for transmitting operation signals from a sample supply control unit 30 are connected to the 3-dimensional drive mechanism 33, the syringe type pump 34, the first and second solenoid valves 36, 37, the liquid delivery pump 35, and the rotary drive mechanism 23 for the sample holder 22.

Next, a reaction disc 41 holds a plurality of reaction cells 42 on its circumference. About 100 to 200 reaction cells 42 are set in the reaction disc 41, and they may be smaller in number. The volume of each reaction cell is about 80 $\mu l$.

The reaction disc 41 is successively rotated by a rotary drive mechanism 44 so that, at the sample feeding position, a location at which the nozzle 32 of the sample pipetter 31 is lowered is aligned with the reaction cell 42 to be supplied with a sample. The reaction disc 41 is constructed as a constant-temperature bath 43 in which constant-temperature water flows in order to keep the temperature of the reaction cells 42 at a predetermined temperature. The lower half of the reaction cells are immersed in the constant-temperature water. The rotary drive mechanism 44 is connected to a reaction disc control unit 40 by a signal line for transmitting operation signals.

Figure 2:
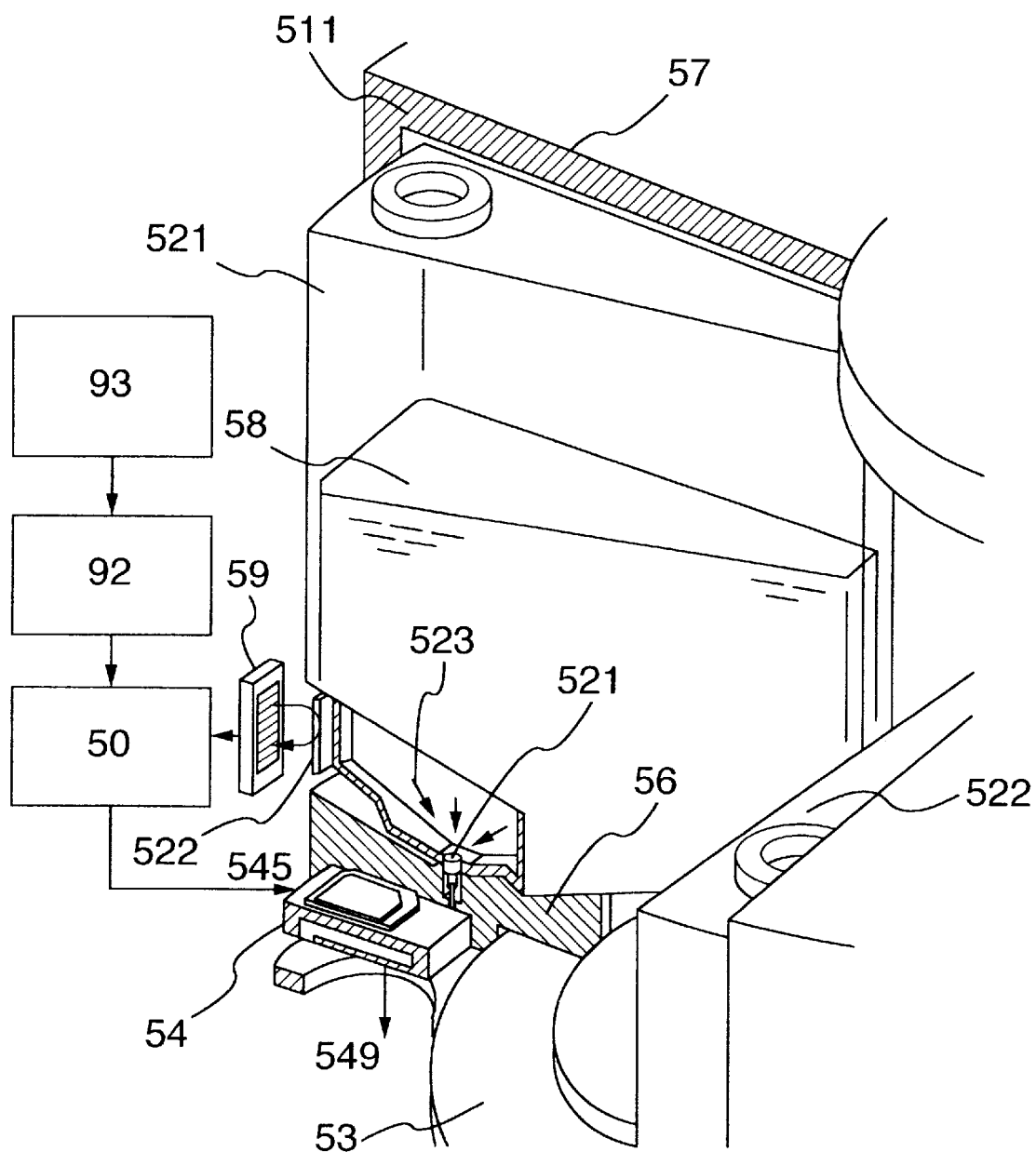
FIG. 2 is a schematic diagram showing the construction of a reagent supply unit according to the present invention.
Figure 3:
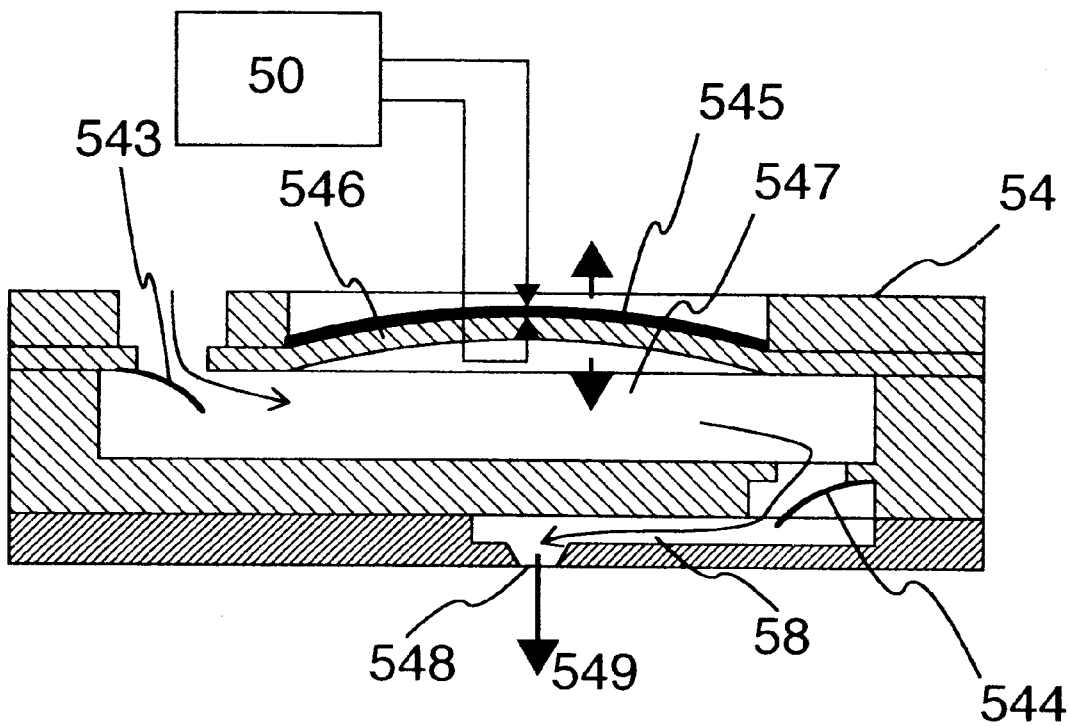
FIG. 3 is a schematic diagram showing the construction of a micropump.

Next, the construction of a first reagent supply unit 511 will be explained by referring to FIGS. 2 and 3 in addition to FIG. 1. FIG. 2 shows the detail of the reagent supply mechanism and FIG. 3 shows a cross section of a micropump shown in FIG. 2. A second reagent supply unit 512 is similar in construction to the first reagent supply unit 511 and thus its explanation is omitted here.

The first reagent supply unit 511 comprises reagent containers 521, a reagent holder 53, micropumps 54, a micropump holder 56, and a reagent holder rotary drive mechanism 55. -The reagent holder 53 is constructed to hold the reagent containers on its circumference around the center axis. One reagent holder 52 can accommodate 40 to 50 reagent containers.

The same number of film type micropumps 54 as the maximum number of the reagent containers 521 that can be held is provided at the bottom of the reagent holder 53 through the micropump holder 56. The micropump holder 56 can be removed from the reagent holder 53 along with the micropumps 54.

The bottom of each reagent container 521 is formed with a connection hole, which is adapted to be connected to the micropump 54 by strongly pressing it against the bottom of the reagent holder 53. The micropumps 54 are each provided with a delivery hole 548 extending vertically downwardly. Hence, the first reagent supply unit 511 and the reaction disc 41 are arranged so that they cross each other on different levels.

The side surface of the reagent containers 521 is provided with a magnetic unit written with data representing the kinds of reagents. At the corresponding circumferential position of the reagent holder 53, a magnetic reader 59 for reading data from the magnetic unit is provided. The signal line from the magnetic reader is connected to a decision unit in a reagent supply control unit 50. The reagent supply control unit 50 drives the micropumps 54 in response to a signal from the magnetic reader 59 and others. The reagent holder 53 is rotated by the reagent holder rotary drive mechanism 55. The reagent containers are accommodated in a refrigerated chamber of the reagent holder 53.

While in this embodiment the magnetic unit is provided on each of the reagent containers, it is also possible to record the kinds and serial numbers of reagents with bar codes, provide a bar code reader on the reagent holder and manage the reagents by the controller 92 or the central signal processor 93.

The micropumps 54 shown in FIG. 3 comprise, from inlet to outlet, an inlet valve 543, a pump chamber 547, a diaphragm 546, a vibration plate 545, an outlet valve 544, and a delivery hole 548. The vibration plate 545 is connected to the reagent supply control unit 50 via a drive signal line. The reagent supply control unit 50 applies an AC voltage signal to both sides of the vibration plate 545. The vibration plate 545 is deformed and vibrated by this signal as shown by thick arrows to vibrate the diaphragm 546 bonded to the vibration plate 545 a required number of times. The vibrations change the pressure in the pump chamber. During the suction stroke the inlet valve is open and the outlet valve closed, and during the delivery stroke these valves assume the reverse states.

Figure 4:
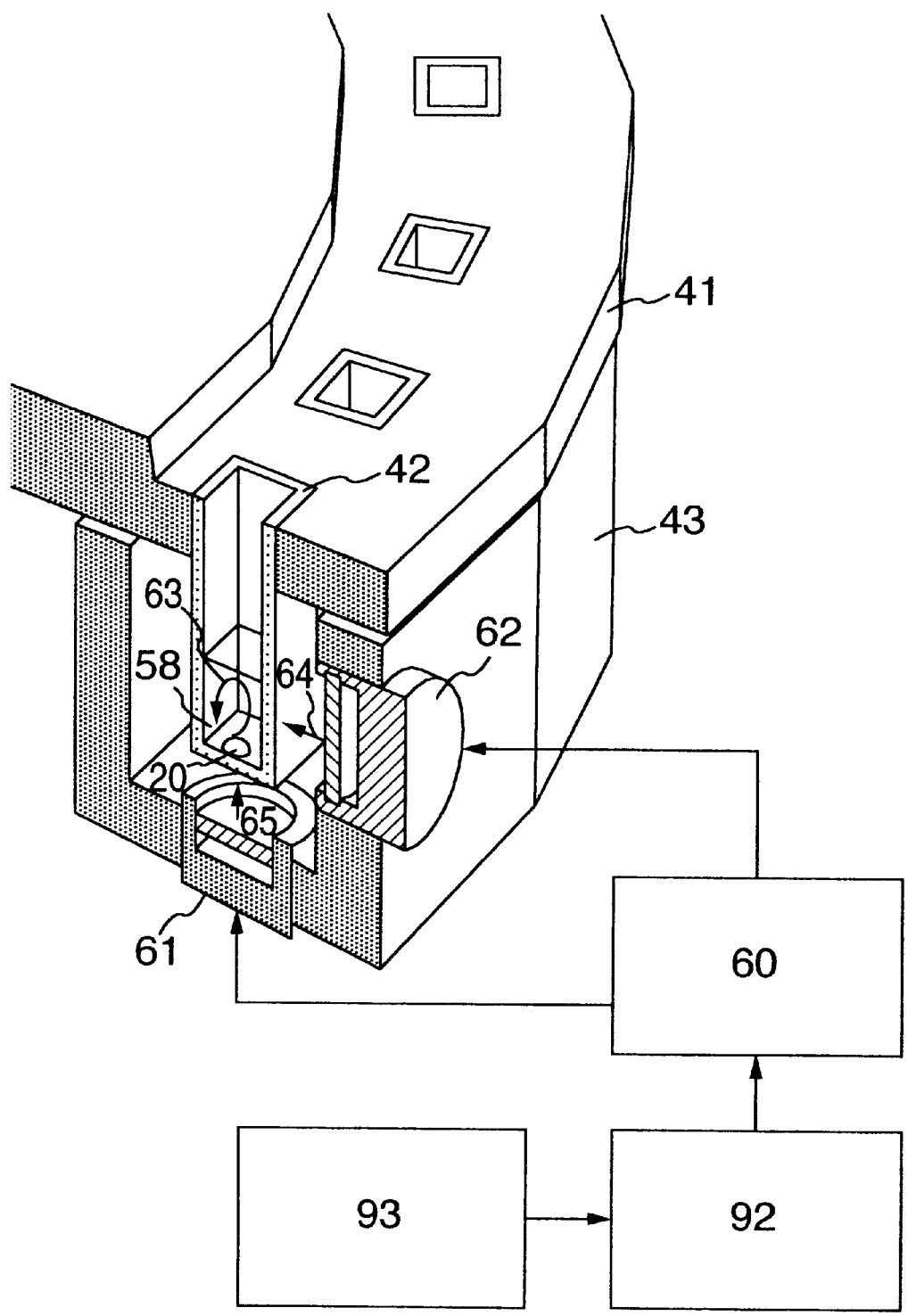
FIG. 4 is a schematic diagram showing the construction of an agitation unit according to the present invention.

Next, the construction of the agitation unit will be described by referring to FIGS. 1 and 4. FIG. 4 shows the detail of an example structure of the agitation mechanism according to the present invention.

This embodiment employs sound waves to implement a non-contact agitation mechanism that does not require cleansing. Other non-contact agitation mechanisms include those that vibrate or rotate the reaction cells themselves.

Sound generating vibration plates 61, 62, which are major elements of the agitation unit, are provided at the bottom and the inner side surface, respectively, of the constant-temperature bath which are at the same positions in the circumferential direction. These vibration plates 61, 62 are connected to the agitation control unit 60 via signal lines through which drive signals are transmitted. As shown in FIG. 1, the vibration plates 61, 62 are arranged below the reaction cells that receive reagents from the first reagent supply unit 511 and the second reagent supply unit 512. By oscillating these vibration plates with signals, sound waves are generated and focused at an area slightly above an intermediate part of the sample liquid to agitate the liquid.

Next, the construction of the spectrophotometer unit will be explained by referring to FIG. 1.

The spectrophotometer unit is provided between the reaction cell cleansing mechanism unit and the sampling position in the circumferential direction of the reaction disc. Inside the constant-temperature bath 43 there are provided a light source 71 and an optical system 72, which are adjusted in position to throw light against the liquid portion of the reaction cells 42. Outside the constant-temperature bath there are an optical system 72 for collecting light that has passed through the reaction cells, a diffraction grating 73 arranged on the extension of the optical system, and a semiconductor optical detector 74 for detecting light that was dispersed by the diffraction grating 73.

For controlling a light detection timing and others and for acquiring a detection signal, a spectrophotometer control unit 70 is connected to the semiconductor optical detector 74 through a signal line. The spectrophotometer unit as the light collecting system and the light detecting system may of course use an optical fiber. There is no problem if a semiconductor light emitting element is used as a light source. It is also possible to use a spiral array sensor and a plane array sensor as a detector.

Figure 5:
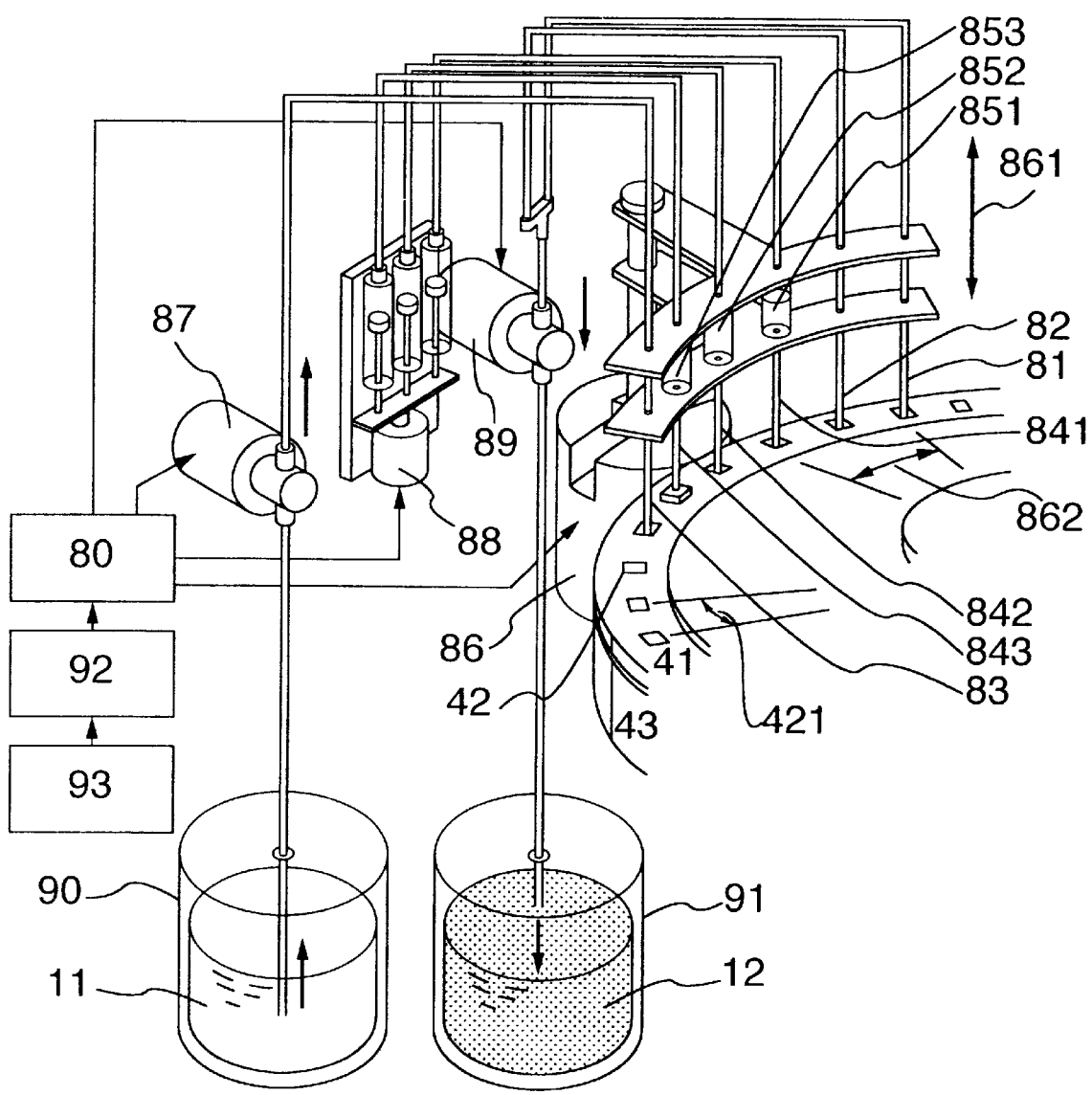
FIG. 5 is a schematic diagram showing the construction of a reaction cell cleansing mechanism according to the present invention.

Next, the construction of the reaction cell cleansing mechanism will be explained by referring to FIGS. 1 and 5. FIG. 5 shows the detail of the reaction cell cleansing mechanism.

The reaction cell cleansing mechanism is arranged behind the second reagent supply unit 512. In this embodiment, it has six washing nozzles, which are, in a counterclockwise order, a concentrated waste liquid suction nozzle 81, a cleansing liquid suction nozzle 82, three cleansing nozzles 841, 842, 843, and a cleansing liquid supply nozzle 83 for supplying a cleansing liquid (pure water).

The concentrated waste liquid suction nozzle 81 and the cleansing liquid suction nozzle 82 are connected to a reaction liquid suction pump 89. The upper ends of the three cleansing nozzles are connected to storage containers 851, 852, 853 that store a cleansing liquid temporarily. A cleansing liquid syringe type pump 88 for temporarily drawing a cleansing liquid into the storage containers and for discharging the cleansing liquid out of the containers is connected to the respective containers through tubes.

The cleansing liquid syringe type pump 88 is integrally formed with the mechanism so that it can be driven by the same mechanism. The pure water supply nozzle 83 connects to a cleansing liquid supply pump 87 that supplies a predetermined amount of cleansing liquid. A cleansing nozzle moving mechanism 86 moves a group of nozzles parallelly in a vertical direction and also in a circumferential direction of the reaction disc by two container positions (see 862 in FIG. 5).

The reaction liquid suction pump, the cleansing liquid syringe type pump, the cleansing nozzle moving mechanism, and the cleansing liquid supply pump are connected to a cleansing mechanism control unit 80 through signal lines. The delivery side of the reaction liquid suction pump 89 is connected to the waste liquid tank 91 and the suction side of the cleansing liquid supply pump 87 is connected to the pure water tank 90.

Signal lines for applying operation signals to the above-described control units for the elements and components are connected to the controller 92, which in turn is connected to the central signal processor 93 via signal lines which issues operation signals for changing the operations according to the items of assay.

Next, the operation of the above construction will be explained according to the operation sequence (1) to (5) shown in FIG. 6.

(1) First, a sample holder rotation mechanism 23 is operated to rotate the sample holder 22 to move the test tubes 21 to a position below the sample pipetter 31. Then, the syringe type pump 34 performs a suction stroke to draw a predetermined amount of sample 20 from the test tube 21 into the nozzle 32 of the sample pipetter 31. Then, after the nozzle 32 is moved to the bottom of the reaction cell 42 by the 3-dimensional drive mechanism 33, the sample is discharged into the reaction cell. The sample pipetter 31 then moves to the washing tank 38 and the first solenoid valve 36 and the second solenoid valve 37 are operated to wash the interior and exterior of the nozzle 32 with the system water. With the cleansing operation finished, the sample pipetter 31 again moves to the position of the sample holder 22 and repeats the same operation.

(2) The reaction cells 42 are rotated by the reaction disc rotary drive mechanism 44 to a position where the first reagent supply unit 511 delivers a reagent. In the first reagent supply unit 511, the reagent holder rotary drive mechanism 55 is operated to position the delivery hole 548 of the micropump 54 directly above the reaction cell 42. When the reaction cell 42 and the delivery hole 548 are aligned, the reagent supply control unit 50 controls the micropump 54 to discharge a predetermined amount of a reagent 58 into the reaction cell 42.

The micropump 54 operates as follows. First, the control unit 50 applies AC signals to the both sides of the vibration plate 545 for a duration corresponding to the number of times that the vibration plate 545 is to be vibrated. In response to this signal application, the vibration plate 545 deflects to vibrate the diaphragm 546. When the diaphragm 546 deflects upward, the inlet valve 543 is opened drawing in the reagent 58. Next, when the diaphragm 546 deflects downward, the outlet valve 544 is opened and the reagent 58 in the pump chamber is discharged. The amount of discharge is about 1–5 $\mu$l for each operation.

The amount of reagent discharged into the reaction cell 42 is proportional to the number of times that the vibration plate 545 is vibrated, and can easily be adjusted by the number of oscillation signals applied from the control unit 50. If the micropump is made by using the micromachining technology, the inner volume of the micropump can be set to 100 $\mu$l or less. This can reduce the amount of reagent that will remain unused at time of shutdown of the apparatus to 100 $\mu$l or less.

In this embodiment, because the micropumps are installed at the bottom of the reagent containers, the reagent needs only to be transferred downwardly and requires no additional head, which in turn allows a simple pump to be used. Further, the reaction disc 41 and the reagent supply unit can be arranged to overlap each other on different levels, realizing a significantly greater space reduction than when they are arranged two-dimensionally. Because the micropump 54 is provided for each reaction cell 42, mutual contamination does not occur between different reagents. Further, because washing is not required each time the reagent is discharged, there is no need to provide additional cleansing means. Because the cleansing liquid is obviated, it is possible to reduce the amount of pure water by about 20 to 30 percent from the amount used by the conventional apparatus.

(3) At the same position where the first reagent has been supplied, the sample and the reagent are mixed in the reaction cell 42 by the agitation unit installed under the reaction cell 42. During or after the supply of reagent, sound waves 64, 65 are radiated from the vibration plates 61, 62 toward the reaction cell 42. The sound waves 64, 65 pass through the wall of the reaction cell 42 and are applied to the liquid therein. When a sound with a strong tendency to propagate straightforwardly is applied to the liquid, a flow 63 is induced in the direction of sound application depending on the sound pressure. This flow mixes the sample 20 and the reagent 58 in the cell. In this method, because no spatulas for stirring are put in the cell, no mutual contamination due to spatulas occurs. Further, there is no need to wash the spatulas every agitation operation and the amount of pure water can be reduced by 60 to 80 percent from that used by the conventional apparatus.

(4) After a series of operations described above is finished, the processing proceeds to the spectrophotometry. The reaction disc is rotated one reaction cell forward from the above position where the sample was first introduced. With the reaction disc rotated, another sample is poured into a subsequent reaction cell which is one cell behind from the previous one, and the similar operation is repeated. As the entire reaction disc is rotated one revolution plus one reaction cell, the first reaction cell's rest position advances one reaction cell at a time. When it is necessary to add a second reagent, the reaction cells that have advanced one reaction cell at a time and reached the second reagent supply position are supplied a predetermined reagent in a manner similar to that in which the first reagent supply unit has performed.

The reagent 58 for reaction and the sample 20 gradually begin to react and produce a color corresponding to the concentration of a component being assayed. As described above, because the rest position of the reaction cells is advanced one cell at a time and, at the same time, all the reaction cells pass the spectrophotometer unit upon each rotary movement, it is possible to measure a change over time of a color as the reaction proceeds. This method is called a rate assay method, which is disclosed in detail in the first conventional technology. The degree of a color produced or the rate of change of a color corresponds to the concentration of a component being assayed.

(5) After repeating the rotation described above, the reaction cells 42 advance to the position of the reaction cell cleansing mechanism. They are advanced one cleansing nozzle upon every rotary movement. During this rotary feed, the reaction cells are washed by a series of nozzles. The cleansing mechanism performs washing in the following manner.

First, the cleansing mechanism is lowered to insert its nozzles into corresponding reaction cells placed below the nozzles. At this time the cleansing liquid supply nozzle 83 discharges unused cleansing liquid. At the same time, other nozzles perform a discharge operation. Then, the cleansing mechanism is raised and parallelly moved circumferentially counterclockwise of the reaction disc 41 by two cells (see 862 in the figure). At the same time, the reaction disc 41 also is rotated one reaction cell counterclockwise (see 421 in the figure). As a result, the nozzles are lowered into the reaction cells which are one cell forward from the previous ones, and all the nozzles except the cleansing liquid supply nozzle 83 perform a suction operation. The nozzles are raised again and then parallelly moved two cells circumferentially clockwise, after which the cleansing liquid supply nozzle 83 discharges unused cleansing liquid and the cleansing liquid nozzles discharge the used cleansing liquid that was previously drawn into the storage containers 851, 852, 853.

As the operation described above is repeated, the cleansing liquid fed from the cleansing liquid supply nozzle 83 is successively carried over to upstream reaction cells and finally drawn into and discarded from the cleansing liquid suction nozzle 82. The first reaction cell to enter this cleansing mechanism has a reacted liquid remaining therein which has already undergone a measurement process. The remaining liquid in this reaction cell is sucked and removed by the first nozzle encountered, i.e., the concentrated waste liquid suction nozzle 81. There is a possibility of the cleansing level becoming degraded by the reuse of the spent cleansing liquid for washing. However, as can be seen from the above operation, because the cleansing liquid that was used to wash a less contaminated reaction cell is used for cleansing a more contaminated reaction cell, there is no fear of further contamination of the reaction cells with the used cleansing liquid. As described above, with a single injection of cleansing liquid the reaction cells can be washed several times, which reduces the required amount of pure water by about 10 percent from that used by the conventional apparatus.

Figure 6:
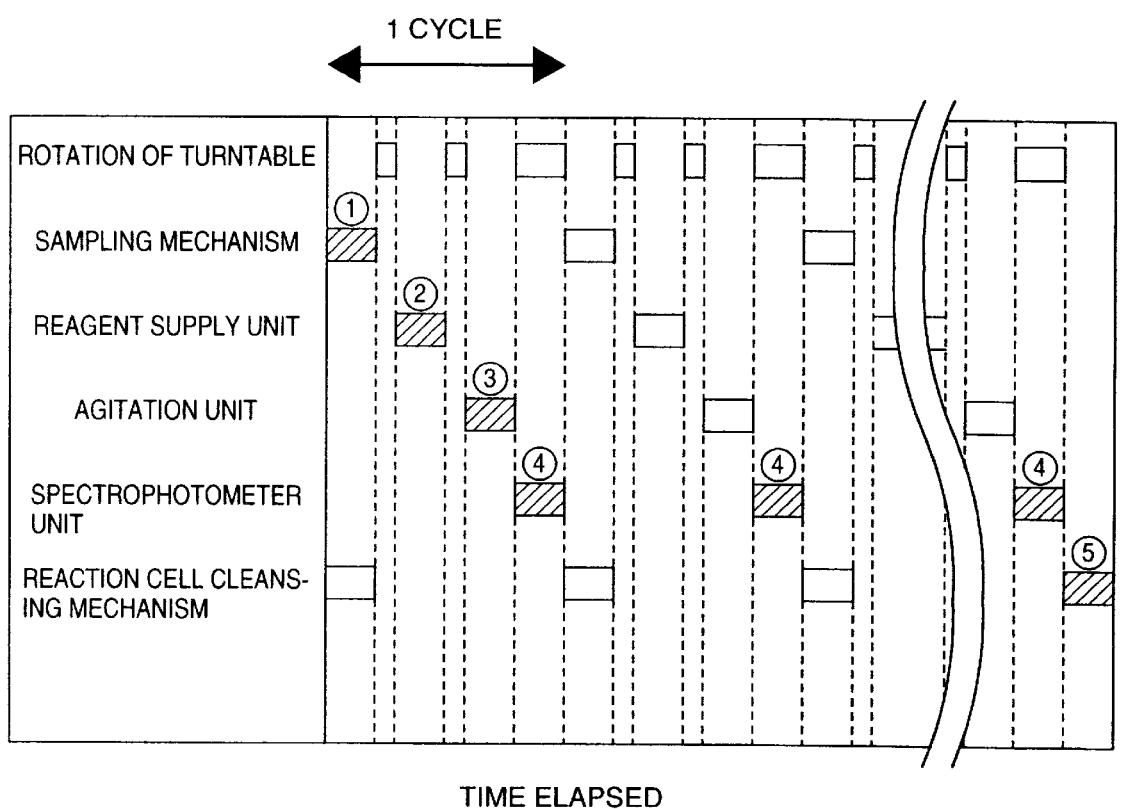
FIG. 6 is a diagram showing a sequence of operations according to the present invention.

As is apparent from the operation sequence shown in FIG. 6, if a reagent is fed into the reaction cell 42 before a sample is injected, no problem arises in terms of operation. In that case, the process (1) and the process (3) in FIG. 6 need only be exchanged.

Figure 7A:
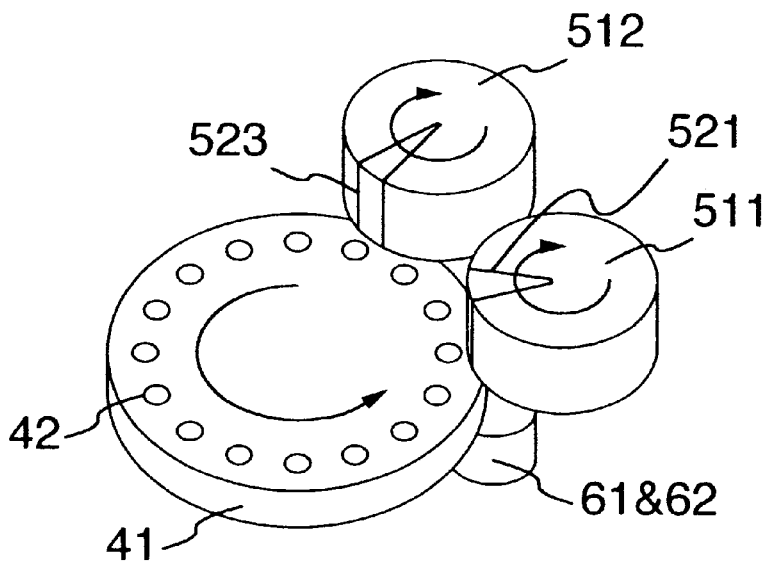
FIGS. 7A and 7B are perspective views showing configurations of another embodiment of the chemical analyzing apparatus.
Figure 7B:
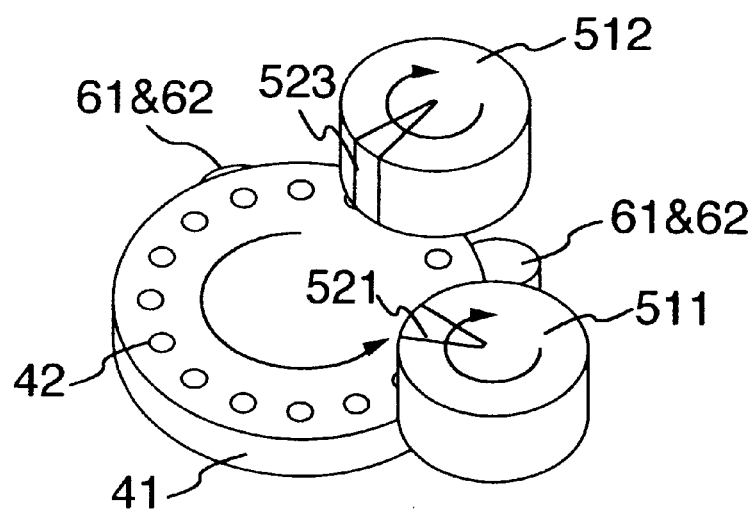

By referring to FIGS. 7 and 8, another embodiment will be described. FIG. 7A schematically shows the reagent supply unit, the agitation unit and the reaction disc in the construction of FIG. 1. The reaction disc is arranged below the reagent supply unit, and the agitation unit is installed below the reagent supply nozzle of the reagent supply unit or at least below the upper surface of the reaction disc. It is of course possible to install the agitation unit other than below the reagent supply unit, as shown in FIG. 7B. In that case, agitation is performed a short time after the reagent is added to the sample. Temperature variations among different parts of the reaction liquid in the reaction cell tends to be eliminated by a forced convection generated by the agitation, so that the reagent in the reaction cell can reach a predetermined temperature quickly.

Figure 8A:
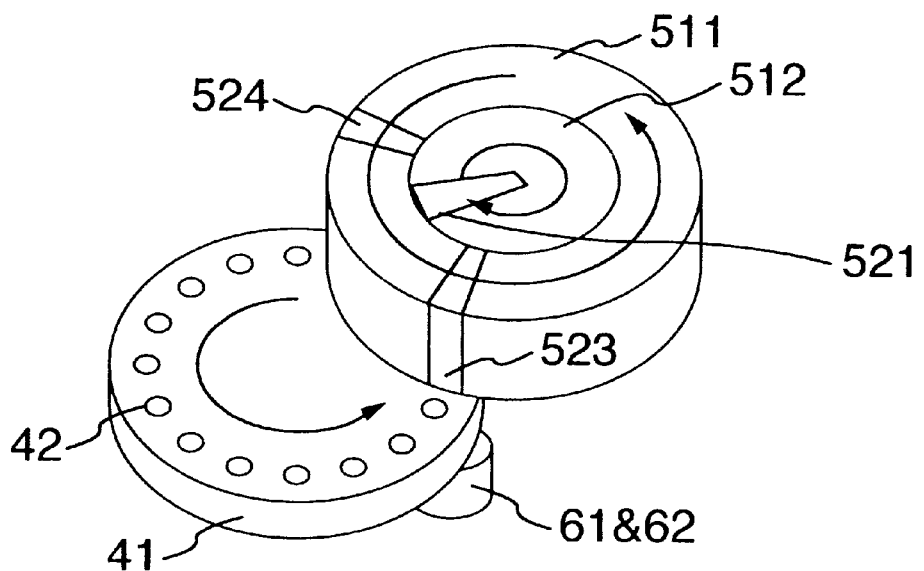
FIGS. 8A and 8B are perspective view showing configurations of another embodiment of the chemical analyzing apparatus.
Figure 8B:
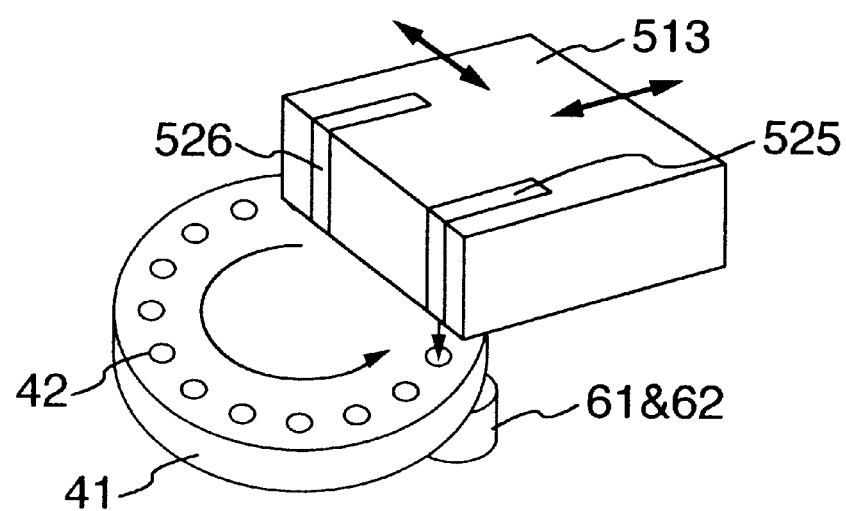

FIG. 8A shows an embodiment in which two concentrically arranged reagent supply units are used as the first and second reagent supply mechanisms. The external reagent supply unit can have two reagent supply points. The amount of overlap between the reaction disc 41 and the reagent supply unit increases, improving space reduction. In the reagent supply unit of the above examples, explanation has been given mainly to the construction in which the reaction disc is rotated for positional transfer of reagent containers. It is of course possible to move the reagent cells to a predetermined position by using XY stage, as shown in FIG. 8B. In this case, too, the reagent supply unit and the reaction disc can be arranged to overlap each other on different levels, thus contributing to reduced space.

With this embodiment it is not necessary to arrange a row of reagent containers on the same plane as the locus of the reagent pipetting mechanism as it is in the conventional apparatus. This allows the reagent supply unit and the reaction disc to be overlapped on different levels, realizing a reduction in space. Because a dedicated cleansing means is not required for the reagent supply unit and the agitation unit, the number of elements can be reduced which in turn results in a smaller size.

Further, in this embodiment because the reagent supply unit does not use the same supply means in handling different reagents, the mutual contamination between different reagents can be mostly prevented. In the mixing unit, because the sample and the reagent can be mixed from outside the reaction cell without contacting it, contamination by the agitation means can be prevented completely. It is therefore possible to provide a chemical analyzing apparatus with little mutual contamination.

Further, with this embodiment, the reagent supply unit and the agitation unit do not require cleansing liquid at all and the reaction cell cleansing mechanism can perform washing with a small amount of liquid, so that the apparatus as a whole can reduce the amount of pure water used to about one tenth of the water volume used by the conventional apparatus. This obviates the pure water making device installed outside the apparatus as well as associated facilities such as water piping. Hence, the only requirement is to store a container of pure water inside the apparatus, as described in connection with FIG. 1. Further, the cost of replacing filters for the pure water making device is also eliminated.

The present invention makes it possible to provide a chemical analyzing apparatus with small size and space.

Another advantage of the present invention is the ability to provide a chemical analyzing apparatus which can prevent mutual contamination between different reagents.

A third advantage of the present invention is the ability to provide a chemical analyzing apparatus which uses only a small amount of pure water, thus requires no pure water making device and associated facilities outside the apparatus, and obviates the need for periodically replacing filters for the pure water making device as well as additional costs and installation spaces associated with other than the apparatus itself.

What is claimed is:

1. A chemical analyzing apparatus comprising:
   a sample holder for holding a plurality of sample containers; reaction cells;
   a movable reaction cell holder for holding the reaction cells;
   a sample supply mechanism for supplying samples from the sample containers to the reaction cells at a predetermined position;
   a reagent supply mechanism, for supplying reagents to the reaction cells to which the samples were supplied;
   a measuring device for measuring characteristics of the samples in the reaction cells supplied with reagents;
   a reagent container holder provided above the reaction cell holder;
   a plurality of reagent containers held in the reagent container holder;
   a reagent supply mechanism provided beneath each of the reagent containers;
   an agitation mechanism provided outside the reaction cells at a position downstream of where the reagent is supplied and upstream of where the measuring device is installed, the agitation mechanism being adapted to agitate contents in the reaction cells without contacting them; and
   a cleansing mechanism having a plurality of storage containers, the cleansing mechanism enabling discharging of a cleansing liquid into the reaction cells after measurement, cleansing of the reaction cells and sucking and storing of the cleansing liquid used for cleansing the reaction cells in the plurality of storage containers, the cleansing mechanism enabling operation of discharge of the cleansing liquid stored in the storage containers into the reaction cells which are one cell forward from the previously cleansed reaction cells.

2. A chemical analyzing apparatus according to claim 1, wherein the cleansing mechanism has a supply unit, the supply unit uses the cleansing liquid, which was used to cleanse the reaction cells located at one position, as the cleansing liquid for a cleansing process of other reaction cells located at another position.

3. A chemical analyzing apparatus according to claim 1 or 2,
   wherein the movable reaction cell holder includes at least one drive unit for moving the reaction cell holder;
   wherein the reagent container holder includes at least one drive unit for holding and moving the plurality of reagent containers; and
   wherein a movement locus of the reagent supply mechanism that moves according to the movement of the reagent containers and a movement locus of the plurality of reaction cells are arranged to intersect.

4. A chemical analyzing apparatus according to claim 3, wherein at least two of the reagent container holder drive units are provided for each of the reaction cell holder drive units.

5. A chemical analyzing apparatus according to claim 1, wherein the reagent supply mechanism comprises a micropump, which delivers about 1–5 $\mu l$ of reagent into the reaction cells every delivery process.

* * * * *